United States Patent [19]
Krotz

[11] 3,964,992
[45] June 22, 1976

[54] CHAMBER AND PROCESS FOR CROSSED IMMUNOELECTRO-PHORESIS

[75] Inventor: Walter Krotz, Hamburg, Germany

[73] Assignee: Medac Gesellschaft fur klinische Spezialpraparate mbH, Hamburg, Germany

[22] Filed: Dec. 27, 1974

[21] Appl. No.: 536,964

[30] Foreign Application Priority Data
Dec. 31, 1973 Germany............................ 2365284
Oct. 11, 1974 Germany............................ 2448552

[52] U.S. Cl. ...................... 204/299 R; 204/180 R; 204/180 G
[51] Int. Cl.² .................. G01N 27/26; G01N 27/28
[58] Field of Search............. 204/180 R, 180 G, 299

[56] References Cited
UNITED STATES PATENTS

| | | | |
|---|---|---|---|
| 3,255,100 | 6/1966 | Raymond........................ | 204/180 G |
| 3,407,133 | 10/1968 | Oliva et al. ......................... | 204/299 |
| 3,479,265 | 11/1969 | Elevitch......................... | 204/180 G |
| 3,649,499 | 3/1972 | Virtanen et al................. | 204/299 X |
| 3,766,047 | 10/1973 | Elevitch............................. | 204/299 |

OTHER PUBLICATIONS
Groc & Jendrey, "Modifications of Laurell's Crossed Immunoelectrophoresis With Special Gel Chamber," Clinica Chimica Acta, 52, (1974) 59–69.

Giebel and Saechtling "A Combination of Micro–Disc Electrophoresis With Antigen–Antibody Crossed Electrophoresis," Hoppe–Seyler's Z. Physiol. Chem., vol. 354, June, 1973, pp. 673–681.

Primary Examiner—John H. Mack
Assistant Examiner—A. C. Prescott
Attorney, Agent, or Firm—Cushman, Darby & Cushman

[57] ABSTRACT

A chamber and process for performing the electroimmunomigration step (the second phase of a crossed-electrophoresis process) for separating protein-containing biological fluids. The chamber preferably includes a base plate having a well defined therein, a depot subdividing the well into migration and connecting wells, and a device for defining a vertically variable gap in the depot so that a first carrier having a protein-containing sample in the depot is in contact with a second carrier in the migratory well and/or connecting well. Various devices may be provided for particularly defining the gap, and for defining the depot and the areas of the wells adjacent the depot.

19 Claims, 9 Drawing Figures

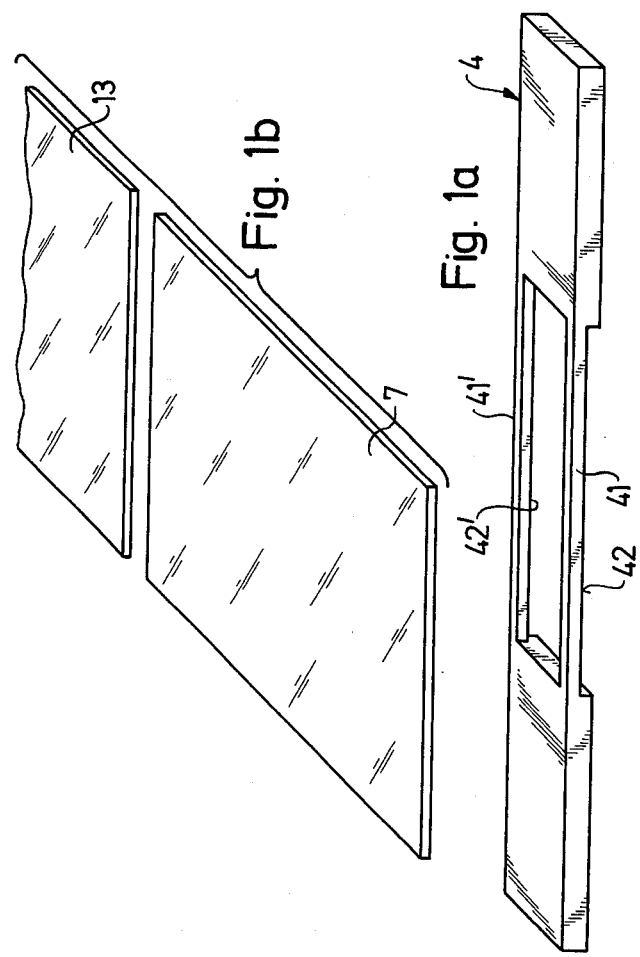

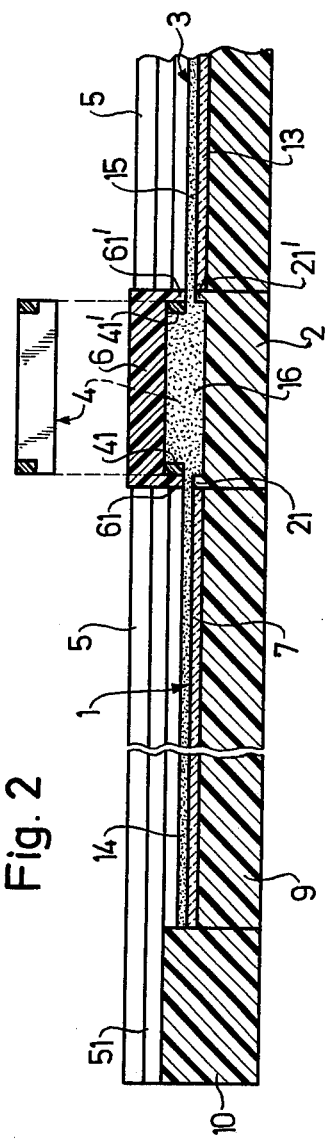
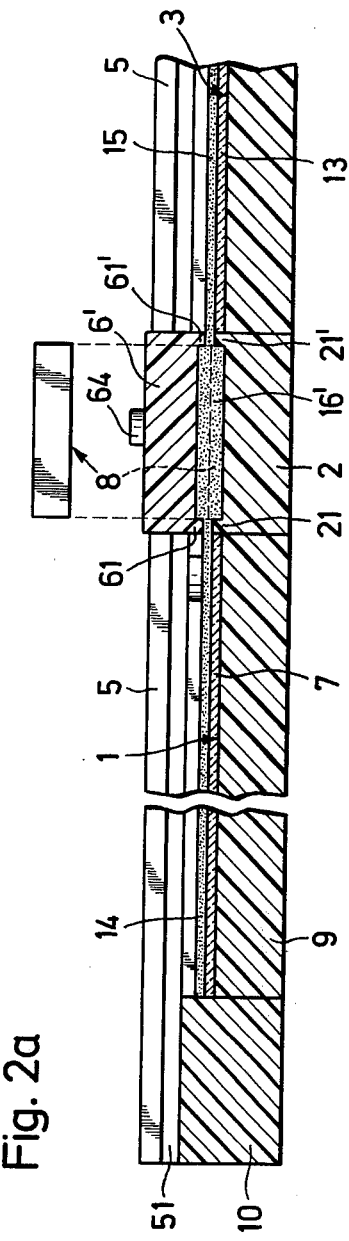
Fig. 2
Fig. 2a

CHAMBER AND PROCESS FOR CROSSED IMMUNOELECTRO-PHORESIS

BACKGROUND AND SUMMARY OF THE INVENTION

Electrophoresis in a suitable carrier, e.g. in agarose, polyacrylamide or starch gel, or alternatively in filter paper or acetate foil is used for separating protein constituents of biological fluids. It is also known that the separation can be considerably improved if following on the electrophoretic preliminary separation in a carrier, immunomigration is subsequently performed at right angles to the first separating direction. This process is called crossed-electrophoresis.

Laurell disc electrophoresis described in Hoppe-Seyler's Z. Physiol. Chem., vol. 354, pp. 673 – 681 (1973) uses a base plate with a well into which the antiserum-containing agarose solution is poured. In the first phase of this process a polyacrylamide gel poured into capillary tubes 5 cm long and with an internal diameter of 1 mm is subjected to micro-disc electrophoresis. These polyacrylamide gel cylinders are pressed into a slit previously cut in the antiserum-containing agarose layer close to one edge of the well. The pressing of the polyacrylamide cylinder into the agarose carrier merely produces a mechanical connection between the two carrier layers. As a result of this solely mechanical contact between the two carriers, the transition of the protein fractions from the first gel to the second is made more difficult.

If the same carrier, e.g. the same gel was used for both crossed-electrophoresis phases, many technical difficulties would admittedly be obviated, but protein separation is not optimum. Furthermore, through the use of different gels, it is possible to combine their individual advantages but then considerable technical problems occur resulting from the fact that the second gel has to be poured onto the first gel to permit the transition of the protein fractions into the second gel. Due to the differing endosmosis in different gels, a waterflow occurs at the interface which impairs or completely prevents the further migration of antigens. Due to the varying drying characteristics of different gels (e.g. agarose gels dry out whereas polyacrylamide gels shrink) a separation of the gels can easily occur at the interface. In addition, different gels have different optimum layer thicknesses which also makes it more difficult to combine different gels.

The problem of the present invention is to develop a suitable chamber for performing the second crossed-eletrophoresis phase preferably using different carriers or gels for the electrophoresis step and the electroimmunomigration step, in order in this way to utilise the advantages of different gels during separation. In addition, a process for performing the electroimmunomigration step using the novel chamber is proposed.

Therefore the object of the invention is a chamber for the second crossed-electrophoresis step following on the prior electrophoretic separation of a protein-containing sample in a first carrier, accompanied by separation in a second carrier in a direction at right angles to the first separating direction, which comprises a base plate with a well for a second carrier, wherein the well in the base plate is subdivided into a migration well and a connecting well by a depot for receiving the first carrier, whereby a lid is provided for the depot which in each case provides a vertically variable slit, via which the first carrier in the depot is in contact with the second carrier in the wells.

This chamber, which will be described in greater detail hereinafter, makes it possible for the first time to satisfactorily perform electroimmunomigration in a technically uncomplicated manner in a carrier differing from that used for the previous electrophoresis. For example, a protein-containing biological sample can firstly be separated by means of conventional disc-electrophoresis or by means of flat disc-electrophoresis using a polyacrylamide gel. The particular advantage of a polyacrylamide gel is its concentration effect so that even small quantities of low protein fluids can be investigated, e.g. body fluids of small test animals (rats, mice, chickens, etc.) or the cerebrospinal fluid of humans. Thus it is possible to work with very small quantities of test fluid which obviates any prior concentration which can easily lead to denaturing of certain antigens.

The second phase, i.e. electroimmunomigration, can be performed using the chamber according to the invention in a different gel, e.g. in conventional agarose gel, wherein much better defined precipitates are obtained than in polyacrylamide gel. The optimum layer thickness for agarose gel is admittedly about 1 mm, but in the novel chamber this layer can without difficulty be poured onto the polyacrylamide gel, although the layer thickness of the latter is generally a few millimetres, preferably approximately 3 mm. It has surprisingly been found that the vertically variable slit by means of which the two different gels are in contact is adequate, and it has been found that substantially all the antigens pass from the first gel into the second gel. Thus, improved protein analysis is possible using extremely small quantities of test fluid with low antigen concentration leading to a representation of the antigens in the form of well-defined precipitate peaks.

It is often more advantageous to use cellulose-acetate membrane foils in place of the polyacrylamide gel as the first carrier. They have proved particularly suitable for protein electrophoresis and are at present the most frequently used carrier material for this purpose in clinical chemical laboratories. Cellulose-acetate foils are also a very suitable carrier medium for immunodiffusion methods and immunoelectrophoresis. Agarose is best suited as the carrier material for the second phase of crossed-immunoelectrophoresis with its various modifications, whereas for the second phase of crossed-immunoelectrophoresis cellulose-acetate membrane foil can without difficulty be used as the carrier material. In the second phase considerable difficulties occur because evaporation leads to drying or shrinkage of the foil. It is substantially impossible to work with an intermediate layer.

In the chamber according to the invention these difficulties can be obviated in that the depot lid has holes in the area adjacent to the migration well. Warm agarose can be poured through one of these holes onto the cellulose-acetate strips in the closed depot obtained in the first crossed-electrophoresis step, so that the cellulose acetate membrane foil is embedded in agarose and evaporation with its consequences is prevented.

According to a further embodiment of the chamber of the invention, a plurality of individual chambers is combined to form a multiple chamber. This permits the simultaneous performance of the second crossed-electrophoresis step with a plurality of carriers used in the first separating step.

BRIEF DESCRIPTION OF THE DRAWINGS

The chamber according to the invention is explained hereinafter relative to the drawings, wherein show:

FIG. 1a is a perspective detail view of an alternative embodiment of a spacer that may be used in the chamber of FIG. 1;

FIG. 1b is a perspective detail view of glass plates that may be used in the migratory and connecting wells of the chamber shown in FIG. 1;

FIG. 2 is a sectional view of the chamber of FIG. 1 taken along lines II—II thereof, showing the chamber filled;

FIG. 2a is a sectional view of the chamber of FIG. 1c taken along lines II—II thereof, showing the chamber filled;

DETAILED DESCRIPTION OF THE DRAWINGS

Figure 1:
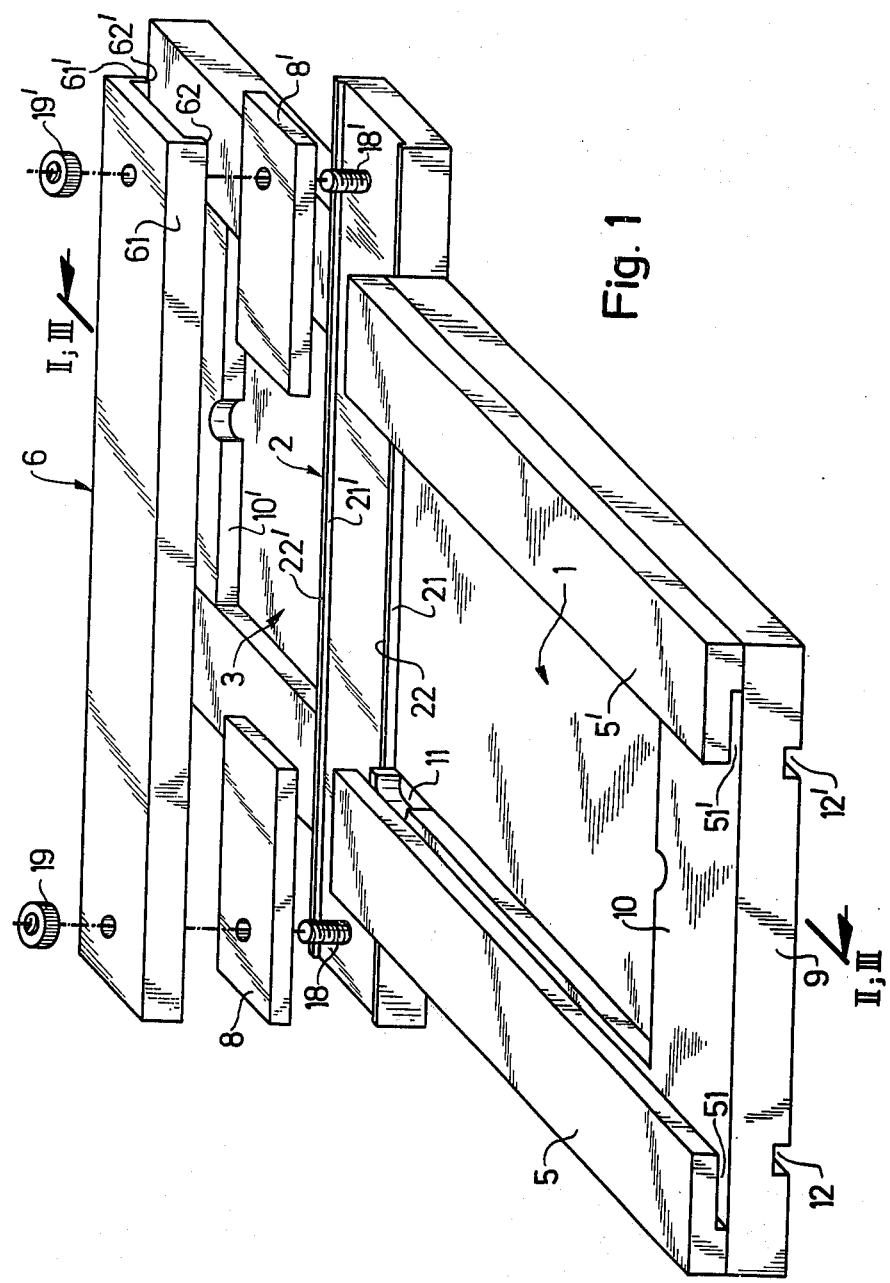
FIG. 1 is an exploded perspective view of an exemplary chamber according to the present invention.

The chamber comprises a base plate 9, which on all four sides is surrounded by a frame 5, 5', 10, 10' so that at the top a well-like depression is formed in the centre. This depression is subdivided into a migration well 1 and a connecting well 3, wherein working takes place with the second gel 14, 15. Between wells 1 and 3 is located depot 2 for receiving the first gel 16 which already contains the antigen sample separated in the previous step by electrophoresis. In order to protect the first gel 16 against drying, a lid 6 is provided which is secured in the edge area by appropriate fastening means, for example screws 18, 18' with knurled or wing nuts 19, 19'.

Suitable spacers are placed between depot 2 and lid 6. The shape of the spacers depends, inter alia, on the electrophoresis method used in the first step. When performing a conventional disc-electrophoresis process, a gel cylinder is obtained and spacer 4 (FIG. 1a) is intended to receive the same, whereby its two lateral spacer portions are interconnected by two webs 41 and 41'. These webs laterally delimit the depot volume in such a way that on mounting lid 6, gel cylinder 16 is pressed flat between the lower depot portion 2 and lid 6 (FIG. 2). Webs 41 and 41' do not extend downwards to the surface of depot 2 so that a gap is left enabling the second gel 14, 15 poured into migration well 1 and connecting well 3 to reach first gel 16.

Figure 3:
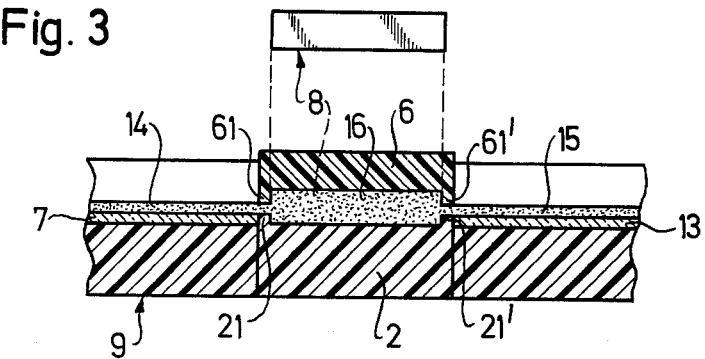
FIGS. 3 and 3a are sectional views taken along lines III—III of FIG. 1 showing various modifications of the chamber according to the present invention, the chamber being full.
Figure 3A:
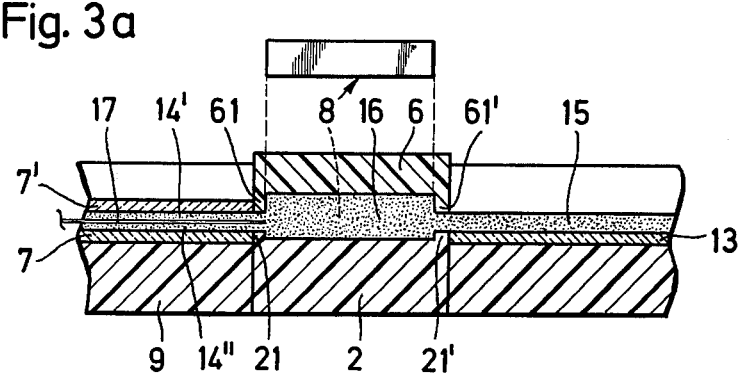

If in the first step flat disc-electrophoresis is used for separating the sample, spacers 8 and 8' (FIG. 1) are used which leave free the central portion of depot 2. In the case of flat disc-electrophoresis, a flat parallelepiped gel slab is obtained which is placed as such on depot 2 and can be covered with lid 6 (FIG. 3).

The height of spacers 8 and 8' or the lateral portions of spacer 4 in each case determine the height of the slit between surfaces 22 and 22' the lateral webs 21 and 21' of depot 2 and the lower interfaces 62 and 62' of lateral web 61 and 61' of U-shaped lid 6. The first gel 16 and the second gel 14, 15 in the chamber comes into contact with one another via these gaps. The under-edges 42 and 42' of spacer 4 are preferably aligned with the lower edges 62 and 62' of lid 6.

The width of lid 6 preferably corresponds to the width of depot 2 so that the lateral webs 21 and 21' of the depot as well as 61 and 61' of the lid determine the height of the gaps contiguous with migration well 1 and connecting well 3. The height of these gaps depends on the gels used and the layer thicknesses thereof. Conventionally the height is between 0.5 and 1.0 mm and is in particular 0.7 mm if the first gel 16 is a polyacrylamide gel with a height of about 3 mm and the second gel an agarose gel with a layer thickness of about 1 mm.

Migration well 1 is preferably sufficiently deep to receive a glass plate 7 which covers its whole surface. The second gel is poured onto this glass plate 7 so that it can easily be removed from the chamber at the end of electroimmunomigration. A glass plate 13 can optionally also be provided for connecting well 3. The glass plates 7 and 13 are approximately sufficiently thick to enable alignment of their surfaces with the upper edges 22, 22' of lateral webs 21, 21' of depot 2.

When pouring the second gel 14 into migration well 1, an undesired accumulation of gel can occur adjacent to depot 2 which due to differing layer thicknesses would lead to values which could not accurately be reproduced. Therefore in the area of depot 2 overflow outlets 11 are provided on the edge of migration well 1 which are connected with discharge channels 12, 12' on the underside of base plate 9. This insures that the gel layer in migration well 1 has a uniform layer thickness.

If due to its chemical characteristics the second gel does not polymerise in air but only in a closed chamber, the migration well 1 must be sealable. To this end horizontal slits 51 and 51' are provided on the sides of migration well 1 in frame members 5 and 5', whereby a not shown cover plate can be inserted into the said slits. As a result a closed gel chamber is obtained wherein can, for example, be polymerized a polyacrylamide which does not gel in air.

Figure 1C:
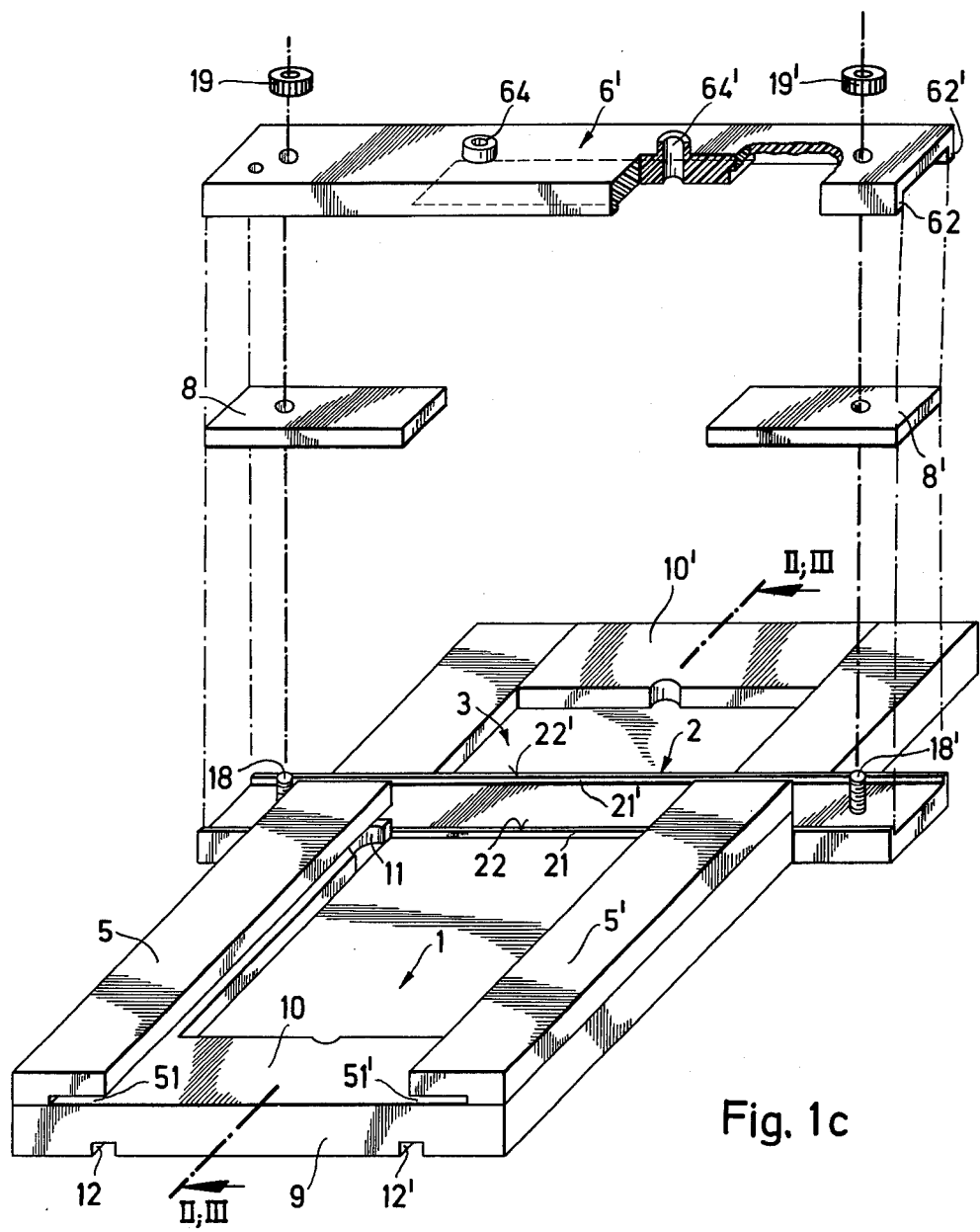
FIG. 1c is an exploded perspective view of an alternative exemplary embodiment of the chamber according to the present invention.

FIG. 1c shows the chamber according to the invention with a different construction of lid 6' for depot 2. Lid 6' serves to protect the first carrier 16' (FIG. 2a), for example a cellulose-acetate membrane foil embedded in agarose gel against drying and shrinkage, and is secured in the edge area of depot 2 by means of suitable fastening means 18, 19 and 18', 19'.

Suitable spacers 8, 8' are placed between depot 2 and lid 6'. Lid 6' has a U-shaped groove which is about 0.5 mm deep in the area adjacent to migration well 1. With the lid mounted and screwed down, the height of the gap between depot 2 and lid 6' is normally between 0.5 and 1.0 mm, and is more particularly 0.7 mm if the first carrier is a cellulose-acetate membrane foil embedded in agarose gel with a layer thickness of about 0.10 to 0.15 mm and the second carrier is an agarose gel with a layer thickness of about 1 mm. In the area adjacent to migration well 1, lid 6' has holes 64, 64' which serve for introducing warm agarose into depot 2 and for the escape of air from the depot. If the cellulose-acetate membrane foils used in the first phase of crossed-immunoelectrophoresis are to be used in conjunction with antibody-containing agarose in the subsequent second phase, then in order to prevent evporation with its consequences (shrinkage and drying) for the first carrier about 1 ml of hot agarose is pipetted onto the bottom of depot 2, allowed to cool, and immediately on conclusion of the first crossed-electrophoresis phase the appropriately cut cellulose-acetate strips are placed on the agarose gel layer. Lid 6' is placed on the depot, screwed shut and 1% warm agarose at 52°C is passed through one of the holes, e.g. hole 64 into the depot. The air displaced by the agarose introduced escapes through a different hole, e.g. hole 64'. When working with agarose whose setting point is below 45°C, a cooling device is switched on beforehand and only then is the connecting well 3 and the gap between depot 2 and the antibody-containing carrier, e.g. agarose gel in migration well 1 filled with agarose at max. 56°C.

FIG. 3 shows the use of carrier plates 7, 7' which are, for example, coated with antibody-containing agarose gel 14', 14''. For example, one of the plates can contain a polyvalent antiserum and the other a monospecific antiserum. After the gel layers have solidified, one of the gel plates is for example covered with a thin impermeable layer 17, for example a correspondingly cut-to-size plastic foil. On the thus prepared first glass plate 7 is now placed a second plate 7' with the gel layer downwards and which accurately covers the first plate 7. Prior to placing together the two plates, from the cathode side of the two gel layers 14', 14'' a 3 mm wide gel strip is cut off and removed over the entire length, and from the anode side a 6 mm wide gel strip is cut off and removed. On the cathode side this free space is used to receive antiserum-free agarose at 52°C. After the poured on antiserum-free agarose has set with the aid thereof a continuous connection to the first carrier 16, for example, polyacrylamide, agarose or cellulose-acetate strips with the antigens separated in the first phase is produced. On the anode side the free space serves to receive the filter paper bridge which forms the connection with the electrode tank. The thickness of glass plates 7, 7' and the gel layers 14', 14'' located thereon is preferably selected in such a way that the plastic foil 17 located therebetween comes to rest at half the height of the longitudinal slit of depot 2. The second phase of crossed-immunoelectrophoresis is now performed. A further processing of the pherograms takes place in conventional manner, i.e. pressing out, drying and staining.

Figure 4:
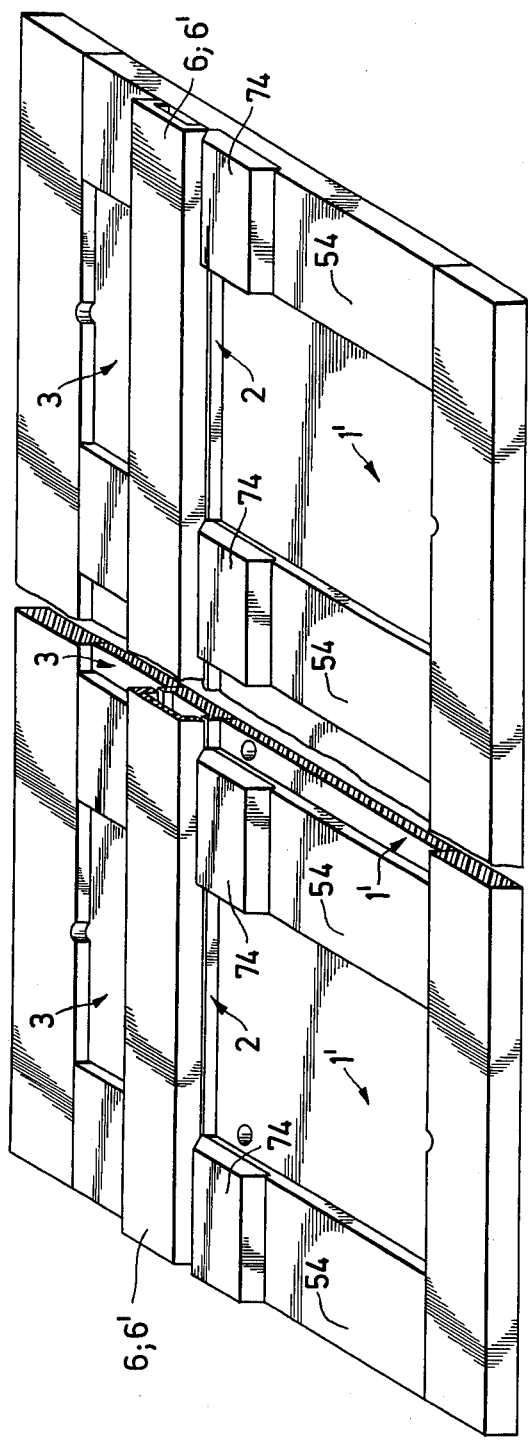
FIG. 4 is a perspective view of an exemplary multiple chamber assembly according to the present invention.

FIG. 4 shows the combination of the individual chambers to form a multiple chamber. The number of individual chambers is determined by the laboratory conditions. In the second crossed-electrophoresis step, in each case several samples can be simultaneously separated in the migration wells 1' subdivided by webs 54. Advantageously depot 2, and depending on the type of operation, lid 6 or 6' is made continuous over the entire width of the multiple chamber. Holding pieces 74 serve to clamp a correspondingly cut-to-size plastic foil which as an impermeable layer can be used to separate two carriers in migration well 1'. A plastic foil provided with extensions in this way can be removed more easily from the migration well 1' after performing the process of the invention.

The object of the invention is also a process for performing crossed-electrophoresis using the chamber which has been described hereinbefore, wherein the first carrier containing the protein sample operated by means of disc- or flat disc-electrophoresis is placed in the depot of the chamber, whereby a second carrier is placed in the migration well and optionally in the connecting well so that the carriers are in contact with one another through the gap between depot and depot lid, and between the ends of the wells remote from the depot an electrical voltage difference is produced so that the protein constituents are separated in the second carrier at right angles to the separating direction in the first carrier, and are optionally precipitated. To produce precipitates in the second carrier advantageously an antiserum is added thereto in the migration well.

When using gels as the carrier a strip of about 0.4 to 0.8 cm, preferably 0.6 cm of the second gel is left in the migration well immediately adjacent to the depot for the first gel, free from antiserum in order to prevent a migration thereof into the first gel in the opposite direction. This can, for example, take place in that initially the entire surface area of the migration well is filled with antiserum-containing gel, and after it has gelled a narrow strip is cut out from the side adjacent to the depot and is replaced by antiserum-free gel.

The process can also be performed by using as carriers gels which are already known for crossed-electrophoresis, e.g. starch, polyacrylamide or agarose gels. The prior separation and the first crossed-electrophoresis phase can also take place on filter paper or acetate foil, whereby using the special chamber according to the invention the second phase, i.e. electroimmuno-migration is performed, e.g. in agarose gel. According to a particularly preferred embodiment, in the first step, i.e. disc or flat disc-electrophoresis a polyacrylamide gel is used, whereas in the second step agarose gel is used. The layer thickness for the polyacrylamide gel in the depot is then about 3 mm and the layer thickness for the agarose gel in the migration well about 1 mm in the case of the chamber according to the invention. Due to the special construction of the chamber according to the invention these optimum layer thicknesses for the different gels can be combined with one another without difficulty.

When performing the process according to the invention, the antigen sample to be investigated is initially separated by using a conventional disc-electrophoresis or flat disc-electrophoresis process. Suitable equipment is already commercially available, e.g. from the Desaga Company, Heidelberg. According to the preferred embodiment, in the first step a polyacrylamide gel is used (e.g. pH 8.9, 7.5%, average pore diameter cf. H. R. Maurer, Disc-electrophoresis, Berlin 1968, page 42). When performing flat disc-electrophoresis a gel strip of for example 6.0 cm long, 1.3 cm wide and 0.3 cm high is obtained which contains the sample separated in the longitudinal direction of the gel strip.

After removing lid 6 in depot 2, this strip is placed in the chamber according to the invention between the two spacers 8 and 8'. Subsequently lid 6 is mounted and screwed down with the spacers.

A glass plate 13 covering the whole surface area of the well is placed in connecting well 3. Then 2% agarose at 50°C is poured into the connecting well. An immunomigration gel plate is prepared for migration well 1 by coating glass plate 7 with an antiserum-containing agarose gel in a well. The antiserum used depends on the type of investigation and examples of antisera are e.g. rabbit-immunoglobulin (e.g. Dakopatts Code No. 100 SS), anti-rat serum from rabbits (Behringwerke AG), anti-γ-G-globulin-serum from rabbits (Behringwerke AG) or anti-haptoglobin serum from rabbits (Behringwerke AG). After gelling of the gel, an approximately 6 mm wide strip is removed from one narrow side of the glass plate. The glass plate prepared in this way is placed in migration well 1 of the chamber, and namely in such a way that the agarose gel-free edge is contiguous with depot 2. The free space between the depot edge and the migration gel layer is now filled with agarose at 50°C. An accumulation of agarose in the corners of the two chamber walls between gel depot 2 and the adjacent migration well is avoided in that the excess agarose can flow away through the overflow outlets 11 and be drained away by outflow channels 12, 12' on the underside of the chamber.

After pouring on agarose there is a continuous connection on both sides of depot 2 between the agarose gel in connecting well 3, the polyacrylamide gel with the antigen sample in depot 2 and the immunomigration gel on glass plate 7 in migration well 1, because the warm fluid agarose passes through the gap on both sides of the depot to reach the polyacrylamide gel.

The thus prepared gel chamber is now placed in an electrophoresis apparatus (available e.g. from the Jena Company, East Germany). A filter paper bridge which has previously been damped with electrode buffer is, in the area of frame portions 10, 10', placed on the agarose gel plates in such a way that it covers with an area of about $6.0 \times 1.0$ cm the connecting gel layer on one side and the migration gel layer on the other side. The two other ends of the filter paper bridges are immersed in the electrode vessels of the electrophoresis apparatus which are filled with a buffer solution, e.g. a barbitone buffer, pH 8.6 and ionic strength 0.02.

Bu applying an electrical field (with the chamber size described 3 mA/60 V per chamber) electroimmunomigration is performed at +4°C. When it is terminated the gel chamber is removed from the electrophoresis apparatus. Using a scalpel for cutting purposes, the gel layers adhering to the edges of connecting well 3 and migration well 1, as well as to webs 21, 21' of gel depot 2, are detached and removed by inserting a flat spatula underneath them. The connecting gel plate is discarded, whilst the antigen and antibody portions which have not precipitated after electroimmunomigration are removed from the migration gel plate by washing or squeezing. The gel layer is then dried with hot air. The immunoprecipitates are stained with protein dyes (e.g. Coomassie Blue R) and subsequently evaluated qualitatively and quantitatively. In addition to the migration gel plate, it is also possible to stain for checking purposes the gel strip or cylinder in depot 2 in order to establish whether all the protein fractions have migrated into the migration gel during the electroimmunomigration phase.

The following separations are performed by means of the chamber according to the invention using the process described hereinbefore:

1. 100 microfilters of unconcentrated cerebrospinal fluid were separated into 13 protein fractions.
2. 100 microliters of unconcentrated rat bile were separated into 10 protein fractions.
3. Using a sample quantity of 5 microliters in each case it was possible to demonstrate the four sub-groups of IgG.
4. Using 10 microliters of antigen in each case it was possible to demonstrate the different precipitation patterns of haptoglobin Hp 1—1, Hp 2—1 and Hp 2—2.

These results show that crossed-electrophoresis according to the invention has many uses, particularly when investigating extremely small sample quantities of low-protein body fluids without prior concentration, as well as for the fine separation of protein of biological fluids. The fine separation of haptoglobin provides, inter alia, a new particularly accurate and relatively simply performable method of proving paternity.

According to the invention this process is further developed and improved in that a plurality of antiserum-prepared carriers, in each case separated by an impermeable layer, are placed in the migration well and/or connecting well. According to a preferred embodiment, it is also possible to use carriers prepared with different antisera. Thus in one working process from an electrophoretic separation of the first phase it is possible to obtain several pherograms of the second phase whose peaks can thus be simultaneously located and identified. Using this method, it is also possible to rapidly and easily compare the characteristics of antisera because, for example, coinciding or non-coinciding pherograms are obtained. When investigating gammopaths, as in conventional immunoelectrophoresis each of the gel plates can be prepared with a different dilution stage of the same, e.g. monospecific antiserum.

While the invention has been herein shown and described in what is presently conceived to be the most practical and preferred embodiment, it will be obvious to one of ordinary skill in the art that many modifications may be made thereof within the scope of the invention, which scope should be accorded the broadest interpretation of the appended claims so as to encompass all equivalent structures and procedures.

I claim:
1. A chamber comprising:
   a. a base plate,
   b. means defining a well in said base plate,
   c. means subdividing the well in said base plate into two well portions, a migration well and a connecting well, said well adapted to receive a second carrier for performing a second crossed-electrophoresis step following prior electrophoretic separation of a protein-containing sample in a first carrier, said means for subdividing said well into a migration well and a connecting well including,
   d. a depot, said depot adapted to receive a protein-containing sample in a first carrier for separation in a second carrier in a direction at right angles to a first separating direction of the protein-containing sample,
   e. means defining a vertically variable gap in said depot so that a first carrier in the depot is in contact with a second carrier in the wells, said means including a lid for said depot whereby upon utilization of said chamber with electrophoresis apparatus migration of protein from said sample in said first carrier into said second carrier takes place.
2. A chamber as recited in claim 1 further comprising a glass plate disposed in said migration well.
3. A chamber as recited in claim 2 wherein said depot comprises a U-shaped channel which is defined by a pair of elevated webs each having an upper edge thereof, one web being formed on the portion of the depot adjacent the migrating well, and the other web being formed on the portion of the depot adjacent the connecting well.
4. A chamber as recited in claim 3 wherein the upper edges of the webs are aligned with said glass plate in said migration well.
5. A chamber as recited in claim 3 wherein said lid of said depot includes lateral webs, each of said webs having a lower edge thereof.

6. A chamber as recited in claim 5 wherein said gap is defined between the upper edges of said depot webs and the lower edges of said lateral lid webs, and is about 0.5 to 1.0 mm.

7. A chamber as recited in claim 1 wherein said depot comprises a U-shaped channel which is defined by a pair of elevated webs each having an upper edge thereof, one web being formed on the portion of the depot adjacent the migrating well, and the other web being formed on the portion of the depot adjacent the connecting wall.

8. A chamber as recited in claim 1 wherein said lid comprises a U-shaped channel having the same width as said depot.

9. A chamber as recited in claim 8 wherein said U-shaped channel lid includes a pair of lateral webs, each of said webs having a lower edge thereof, and said webs of said lid adapted to cooperate with said depot to define said gap.

10. A chamber as recited in claim 1 further comprising a pair of spacers, said spacers disposed between said depot and said lid at opposed ends of said depot.

11. A chamber as recited in claim 10 further comprising web means interconnecting said spacers, said web means for reducing the effective width of said depot.

12. A chamber as recited in claim 11 wherein said lid includes a pair of lateral webs, each web having an underedge, and wherein said web means includes a pair of webs having edges, said under-edges of said lid webs being aligned with the under edges of said web means webs.

13. A chamber as recited in claim 1 wherein said migration well has lateral frame portions, and wherein said chamber further comprises means defining horizontally disposed slits in the said lateral frame portions for receiving a cover plate for said migration well.

14. A chamber as recited in claim 1 wherein said migration well is adapted to receive the second carrier in the form of a gel layer 1 to 3 mm high.

15. A chamber as recited in claim 1 wherein said depot is adapted to receive the first carrier in the form of a gel layer 1 to 3 mm high.

16. A chamber as recited in claim 1 further comprising means defining overflow outlets in an upper edge of said migration well adjacent said depot.

17. A chamber as recited in claim 16 further comprising means defining discharge channels on the underside of said base plate, said overflow outlets being connected to said discharge channels.

18. A chamber as recited in claim 1 further comprising means defining holes in said lid in the area of said lid adjacent said migration well.

19. An assembly comprising
a. a plurality of chambers, each of said chambers comprising (i) a base plate, (ii) means defining a well in said base plate, (iii) means subdividing the well in said base plate into two well portions, a migration well and a connecting well, said well adapted to receive a second carrier for performing a second crossed-electrophoresis step following prior electrophoretic separation of a protein-containing sample in a first carrier, said means for subdividing said well into a migration well and a connecting well including, (iv) a depot, said depot adapted to receive a protein-containing sample in a first carrier for separation in a second carrier in a direction at right angles to a first separating direction of the protein-containing sample, (v) means defining a vertically variable gap in said depot so that a first carrier in the depot is in contact with a second carrier in the wells, said means including a lid for said depot whereby upon utilization of said chamber with electrophoresis apparatus migration of protein from said sample in said first carrier into said second carrier takes place, and
b. means for connecting said plurality of chambers together to form a multiple-chambered assembly.

* * * * *